US008477904B2

(12) United States Patent  (10) Patent No.: US 8,477,904 B2
Blaj  (45) Date of Patent: Jul. 2, 2013

(54) X-RAY DIFFRACTION AND COMPUTED TOMOGRAPHY

(75) Inventor: Gabriel Blaj, Almelo (NL)

(73) Assignee: PANalytical B.V., Almelo (NL)

( * ) Notice: Subject to any disclaimer, the term of this patent is extended or adjusted under 35 U.S.C. 154(b) by 298 days.

(21) Appl. No.: 12/968,156

(22) Filed: Dec. 14, 2010

(65) Prior Publication Data

US 2011/0200164 A1  Aug. 18, 2011

(30) Foreign Application Priority Data

Feb. 16, 2010  (EP) .................................. 10153742

(51) Int. Cl.
*G01N 23/207* (2006.01)
(52) U.S. Cl.
USPC ............................... 378/71; 378/81
(58) Field of Classification Search
USPC ..................................... 378/70–90
See application file for complete search history.

(56) References Cited

U.S. PATENT DOCUMENTS

| 7,492,862 B2 | 2/2009 | Bendahan | |
| 2004/0062349 A1 | 4/2004 | Schuster | |
| 2006/0256918 A1* | 11/2006 | Yoneyama et al. | 378/82 |
| 2008/0095311 A1* | 4/2008 | Zheng et al. | 378/71 |
| 2009/0213989 A1 | 8/2009 | Harding | |

OTHER PUBLICATIONS

Quantitative X-ray Spectrometry, Second Edition, Ron Jenkins, R.W. Gould, Dale Gedcke, ISBN 0-8247-9554-7, Marcel Dekker, Inc., New York, 1995.
Pella, P.A. et al., An Analytical Algorithm for Calculation of Spectral Distributions of X-Ray Tubes for Quantitative X-Ray Fluorescence Analysis, X-Ray Spectrometry, vol. 14, No. 3, 1985, pp. 125-134.

* cited by examiner

*Primary Examiner* — Hoon Song
(74) *Attorney, Agent, or Firm* — Leason Ellis LLP

(57) ABSTRACT

An imaging system combines CT and XRD measurements, both measuring the XRD diffraction and the absorption as a function of energy. A goniometer 2, source 4 and two dimensional detector 10 may be used. Embodiments use relatively soft X-rays in the 5-25 keV range. An integrated mounting unit to mount the sample 8 close to detector 10 is also described.

14 Claims, 6 Drawing Sheets

X-RAY DIFFRACTION AND COMPUTED TOMOGRAPHY

FIELD OF INVENTION

The invention relates to an apparatus and a method combining the functions of X-ray diffraction (XRD) and computed tomography (CT).

RELATED ART

Computed tomography (CT) is a technique which combines X-ray images using calculations. Conventional absorption X-ray images of a sample are recorded with the sample in a number of different orientations and the images combined using a computing technique to generate a three-dimensional image of the sample. Such techniques are typically used in either medical or baggage screening applications.

The X-rays used are generally broad spectrum (white) X-rays.

X-ray diffraction (XRD) is a technique that is used for determining properties of a material sample based on the diffraction of X-rays by the material.

XRD measurements may be angle dispersive or energy dispersive. In angle dispersive measurements, a monochromatic beam is used, frequently created using a monochromator, and the XRD measurements made as a function of diffraction angle to probe different length scales in the sample, i.e. different values of the spacing d in the Bragg equation. Conventionally, the angle by which the beam is diffracted is referred to as $2\theta$.

In contrast, energy dispersive XRD uses wide spectrum X-rays and an energy-sensitive detector that can detect not merely the X-ray intensity but the X-ray intensity as a function of energy. The different energies used each correspond to a different length scales in the sample.

A baggage inspection system based on the CT technique has been proposed in US2009/0213989. Further details of the proposed CT system are provided in U.S. Pat. No. 7,492,862. A sample is mounted on a rotating platform and attenuation maps, i.e. conventional X-ray images showing the X-ray absorption across the sample, are taken, and a computed image reconstructed.

The baggage inspection system additionally has an XRD system which brings a region of the sample identified in the CT into alignment with a second radiation source and carries out X-ray diffraction on that region of the sample to establish further information about the region. The system is intended to detect specific high atomic number metals as well as lower atomic number materials such as potentially explosive materials. The system uses hard X-rays, presumably for good penetration, and energy dispersive XRD.

SUMMARY OF INVENTION

In an aspect of the invention, an imaging system may operate in an XRD mode carrying out angle dispersive X-ray diffraction on the sample by measuring the X-ray diffraction as a function of diffraction angle $2\theta$ using the X-ray detector and a CT mode to measure absorption of a sample as a function of position across the sample with the two-dimensional X-ray detector.

By providing an additional CT functionality in XRD apparatus, rather than XRD functionality in CT apparatus, the inventor has realised that it is possible to combine accurate XRD measurements with CT functionality.

In particular, the X-ray source may be a source that emits X-rays having a small number of peaks, for example two, in an energy band in the range 4.5 keV to 25 keV. The two peaks may be closely paced $k\alpha$ and $k\beta$ lines. The source may also emit broad spectrum radiation, such as Bremsstrahlung. In some embodiments, monochromatic X-rays are used with a much lower bandwidth than this, in particular 1% of the nominal energy or better.

The imaging system may be arranged to operate in the CT mode to capture a plurality of absorption measurements of the absorption of the sample as a function of position across the sample by rotating the sample with respect to the source and detector, and to combine the plurality of measured absorption measurements to produce a CT image.

In an embodiment, the apparatus includes an integrated unit comprising the two-dimensional X-ray detector and a rotary sample mount for mounting the sample within 5 cm of the detector.

In another aspect, the invention relates to a method of operation of an apparatus in a CT mode and an angle dispersive XRD mode.

BRIEF DESCRIPTION OF DRAWINGS

For a better understanding of the invention, embodiments will now be described, purely by way of example, with reference to the accompanying drawings, in which.

The figures are schematic and not to scale.

Figure 1:
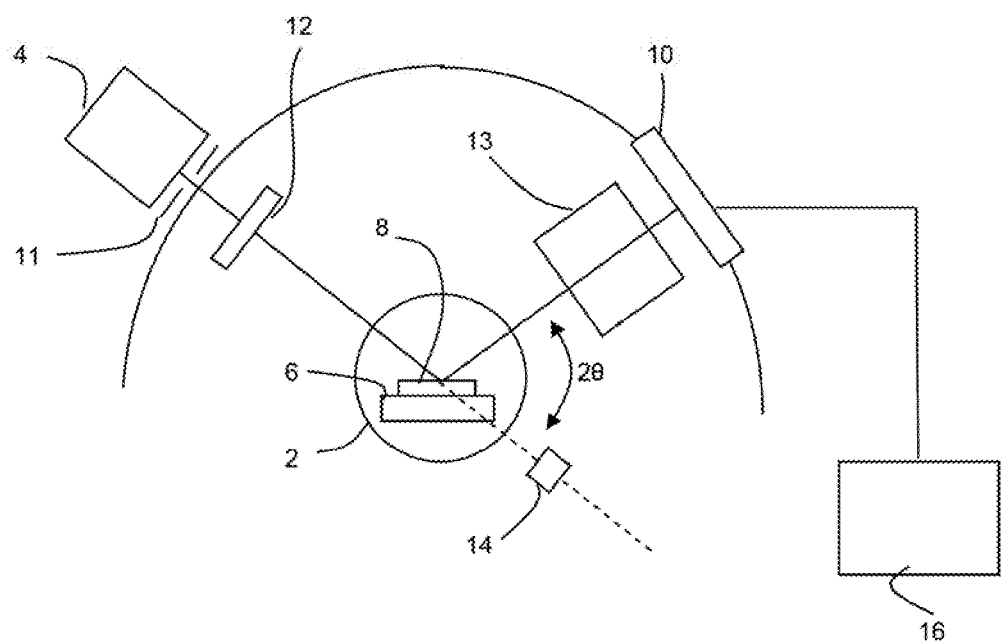
FIG. 1 shows an embodiment of the invention.

Referring to FIG. 1, XRD apparatus used with the present invention uses an angle dispersive XRD arrangement with a goniometer 2 mounting an X-ray source 4, a sample stage 6 for mounting a sample 8 and a two-dimensional photon counting X-ray detector 10. The goniometer can change the relative angles of the X-ray source, 4, sample and X-ray detector. The specific detector 10 used for the measurements presented below is the Panalytical Pixcel (registered trade mark) two-dimensional detector.

In use, the X-ray source provides a monochromatic beam of X-rays at a particular wavelength, and hence energy. The energy is conveniently in the range 5.4 keV to 25 keV which can be achieved using a Cr target for 5.4 keV up to 25 keV with an Ag target. Co, Cu or Mo targets may be used to provide intermediate X-ray energies. The radiation may include Bremsstrahlung radiation together with one or more lines, as will be discussed in more detail below.

A monocromator 12 may be optionally provided to provide truly monochromatic radiation. In this way, highly monochromatic radiation may be used, with the energies varying by no more than 1% from the nominal energy. For example, the monochromator 12 may be used to select a single line from the Cu $K\alpha$ doublet using a Cu source.

Further, a collimator 13 may be provided either between source and sample or between sample and the detector 10, as shown. Where the collimator 13 is provided between the sample and the detector a two-dimensional collimator may be used. A beam conditioner 11 may also be provided as will be discussed below.

To prevent unscattered radiation being incident on the detector, a direct beam absorber 14—i.e. a beam stop—may be provided after the sample in the direct line of the beam of X-rays. This is particularly useful when small diffraction angles 2θ are being used (less than about 5° or 10°).

The radiation is incident on sample 8 and diffracted by an angle 2θ. The two-dimensional detector detects the X-rays diffracted at a plurality of angles 2θ in parallel. To obtain a broader range of angles 2θ, the arrangement of source, sample and detector can be varied using the goniometer.

As will be appreciated by those skilled in the art of X-ray diffraction, additional crystals may be provided to provide additional monochromation and/or additional angular selection to provide higher resolution XRD measurements if required.

So far, the discussion has centred on XRD measurements. The inventors have realised that such an XRD system can also be used for CT measurements.

To carry out CT measurements, the two-dimensional photon-counting detector 10 is used to measure a direct absorption image of the sample, i.e. the absorption of the sample across its area. The direct beam absorber 14 should be removed for this measurement. The sample may then be rotated to different positions, and further direct absorption images taken. Equivalently to rotating the sample, the source and detector may be rotated around the sample instead.

In this configuration, a beam conditioner 11 may be provided at the output of the source 4 to provide a suitable beam. The conditioner may be a pinhole, a slit, an X-ray mirror, X-ray lens or a focussing component such as a capilliary or a fresnel lens for example.

A computer 16 is provided to accept the image data recorded by the detector 10 in both XRD and CT arrangements and to process that data.

The embodiments described use an X-ray source with a target—the preferred embodiments use Cr, Co, Cu, Mo or Ag which typically have the kα and kβ lines in the range 5 to 25 keV. These sources emit broad spectrum (Bremsstrahlung) radiation together with the kα and kβ lines, but in general a substantial amount of the emitted energy is in the kα and kβ lines, typically a doublet.

This energy may be compared, for example, with typical energies around 100 keV dominated by the Bremsstrahlung for typical CT measurements. Indeed, CT measurements can use even higher energies than 100 keV—see for example the range 2 to 20 MeV proposed in US2009/0213989.

Note that when applied to low atomic number elements in a sample, the mechanism that causes X-rays to be absorbed or scattered in the sample varies as a function of energy. To take scattering by carbon as the element in the sample as an example, at low energies the scattering is dominated by the photoelectric effect, caused by the interaction of X-rays with the electrons of the atom. At higher energies, the scattering is dominated by incoherent scattering. Coherent scattering also makes a contribution to absorption of X-rays, though is not the dominant mechanism.

The break-even point where the photoelectric contribution to attenuation equals the incoherent scattering contribution is just above 20 keV for Carbon—above 20 keV the incoherent scattering is more significant than the photoelectric effect and below the photoelectric effects dominates.

The inventors have realised that by probing materials using CT at an energy of 5 to 25 keV where photoelectric effects are significant, it becomes much easier to image samples containing lighter elements and to detect contrasts between elements. In other words, the use of energies below 25 keV has particular benefits for carrying out CT measurements since a different mechanism dominates the scattering of low atomic number elements which can give rise to higher contrast.

Thus, compared with conventional CT, the present invention uses low energy, relatively monochromatic X-rays.

The use of low energy X-rays, also known as soft X-rays, has further advantages for CT. In particular, as well as improved contrast, the higher energy X-rays scatter more, whether from coherent or incoherent scattering, or both, so the use of low energy X-rays allows less scattering and hence better signal to noise ratio.

Further, the use of low energy X-rays allows the use of different detectors to those required for hard X-rays in the conventional CT energy range of around 100 keV or more. A two-dimensional photon counting low noise solid state detector may be used, of a type which is essentially noise free, unlike a charged coupled detector. In particular, embodiments of the invention use the Panalytical Pixcel (Registered Trade Mark) detector, which is a very low noise detector suitable for the 5 to 25 keV energy range.

The use of radiation with monochromatic components also has advantages. A particular problem with CT measurements is the effect known as "beam hardening", in which an X-ray beam is hardened after passing through the sample. This is caused by non-uniform attenuation of different X-ray energies which results in the preferential absorption of X-rays in energy ranges with higher attenuation coefficients, i.e. lower transmission. This causes problems for the CT calculations.

The embodiments described use a source which emits a substantial fraction of the energy (30% or more, 50% or more) in a small number of lines, especially the kα and kβ doublet. The inventors have realised that it is not necessary to go to the difficulty and expense of using a synchrotron to generate X-rays, which generates very highly monochromatic lines indeed but at very high cost. Instead, the type of X-ray source used for XRD using a Cr, Co, Cu, Mo or Ag target is sufficiently monochromatic to provide an improvement with regard to beam hardening over the higher energy sources typically used for CT measurements.

Certain relationships between the size of the source, the pixel size of the detector and the distances between source, detector and sample may be used to provide improved resolution when carrying out CT measurements in this somewhat unusual configuration.

In particular, the inventors have determined that for best resolution CT measurements the distance between the sample and the detector divided by the pixel size should be approximately equal to the distance between the sample and the source divided by the effective size of the X-ray source. Other ratios can be used where required, generally by space considerations, at some cost in resolution.

Accordingly, when using a source with an effective size 0.4 mm by 1.2 mm, using the 1.2 mm in the plane of the diffraction, but a higher resolution pixel detector, with pixels perhaps 50 μm across, the detector should be located very close to the sample—optimally the source would be located about 20 (1.2 mm/0.05 mm) times the distance. The use of the beam conditioner 11 as indicated above can reduce the effective size of the source and so allow the detector-sample distance to be relatively larger. Thus, the beam conditioner is especially useful for the CT measurements but may also be used for the XRD measurements.

In the measurements described below, an algorithm known as "filtered back projection" has been used for the CT calculations, but any algorithm for the CT calculations may be implemented in the computer 16. Such algorithms are known to those skilled in the art and so the details will not be described further.

Figure 2:
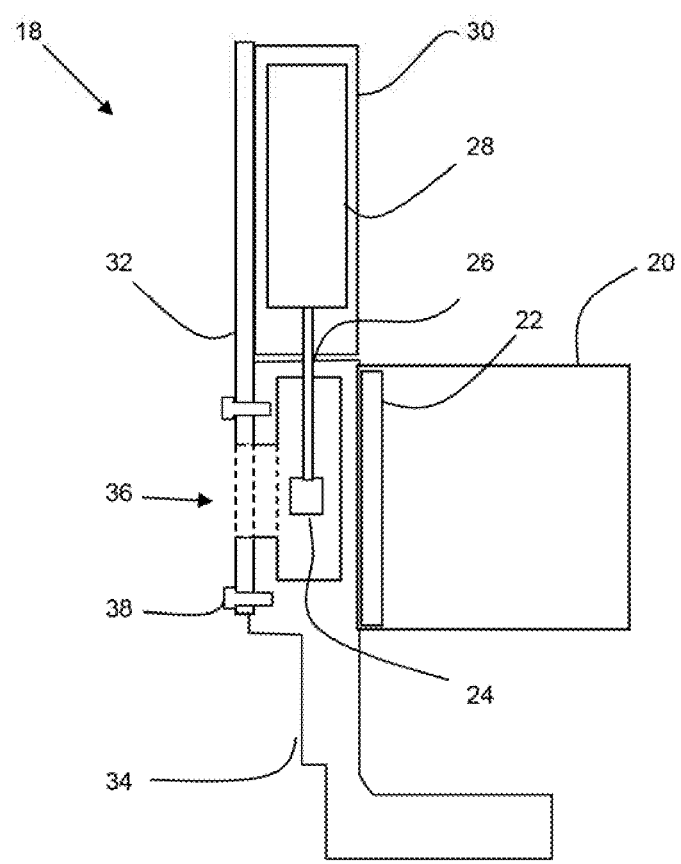
FIG. 2 shows an integrated unit used in another embodiment of the invention.

FIG. 2 illustrates an integrated unit 18 that has been used in a specific embodiment for achieving the mounting of the sample very close to the detector. Detector housing 20 holds a two-dimensional pixel detector 22 and further detector electronics (not shown).

A sample mount 24 which is arranged attached to a rotary drive axle 26 driven by motor 28 contained in motor housing 30. The motor housing 30 is fixedly mounted on mounting plate 32 and this mounting plate 32 and the detector housing 20 are both mounted on mount 34. The mount 34 is then mounted on the goniometer 2. The mount 34 and mounting plate 32 both have an opening 36 at the location indicated by the arrow to allow X-rays to reach the sample directly without passing through the mounting plates. Screws 38 are shown mounting the mounting plate 32 on mount 34—these may be undone to remove the mounting plate 32 together with the motor housing 30, axle 26 and sample mount 24 to allow a sample to be mounted and removed.

The integrated unit is fixed using mount 34.

In this arrangement, the integrated unit 18 is mounted at the centre of the goniometer 2, where the sample is for XRD, and the detector 22 brought close to the integrated unit. Rotation of the sample, especially for CT, may be achieved not by the goniometer 2 but instead by using rotary drive axle 26 driven by motor 28.

In an alternative arrangement, the integrated unit 18 is mounted to the detector 22 with the detector 22 away from the centre of the goniometer. Rotation of the sample is again achieved by using rotary drive axle 26 driven by motor 28. Thus, the integrated unit 18 is a detector and sample mounting unit 18 with an integral sample rotation mechanism. The sample may be held close (typically less than 5 cm, preferably less than 2 cm or even 1 cm) from the detector 22.

Of course, in alternative embodiments, when using a lower resolution detector and a higher resolution source, perhaps with similar sizes, then the source and detector should be located at a similar distance from the sample.

Some benefits of the approach proposed include the savings from having a single apparatus with a single source that can do both XRD and CT measurements of a sample.

Embodiments of the invention are of particular application in a number of fields. In particular, the invention may be of particular use where there are special crystal inclusions in a sample.

One specific area where the embodiments may be useful is in the field of pharmaceutical capsules. The use of CT to examine the pharmaceuticals allows the viewing off the whole volume of the capsule and to analyze and to inspect the entire volume of the sample.

Figure 3:
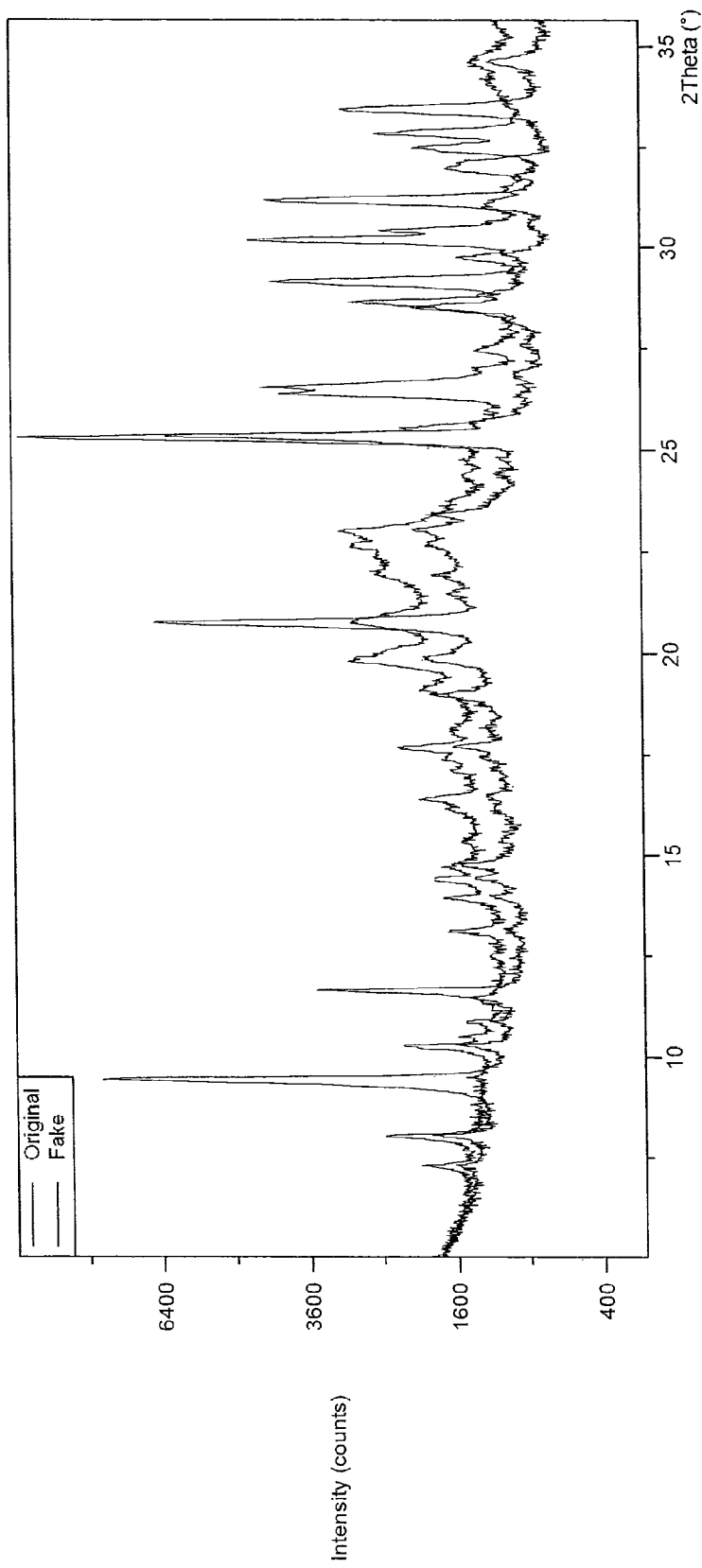
FIG. 3 shows the XRD spectrum taken with a real and a fake sample of a drug.
Figure 4A:
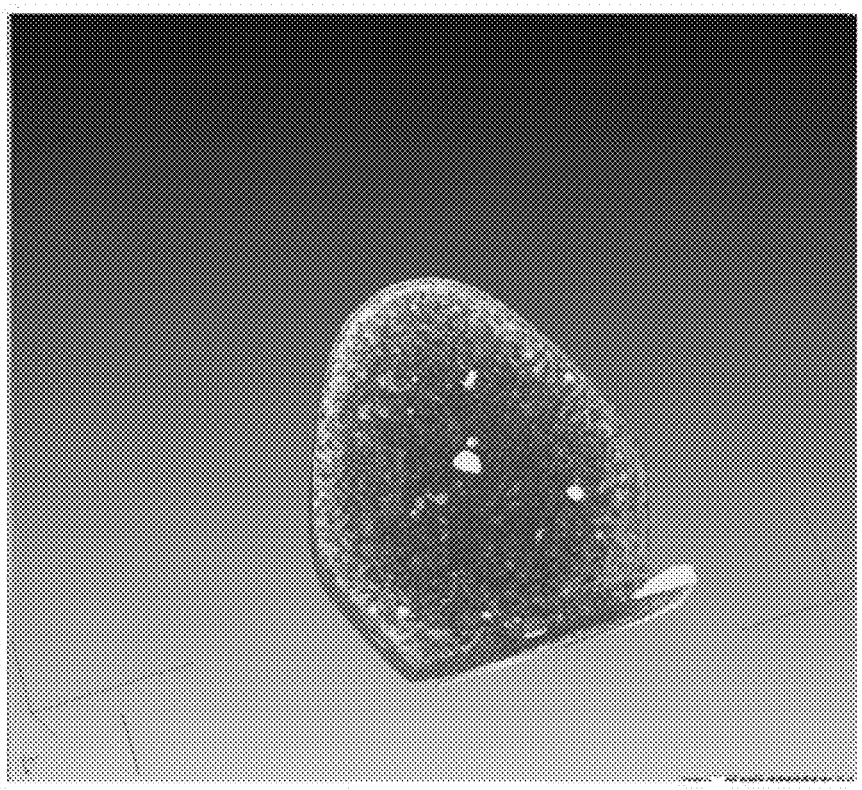
FIGS. 4A and 4b show the CT image of the same samples as in FIG. 3.
Figure 4B:
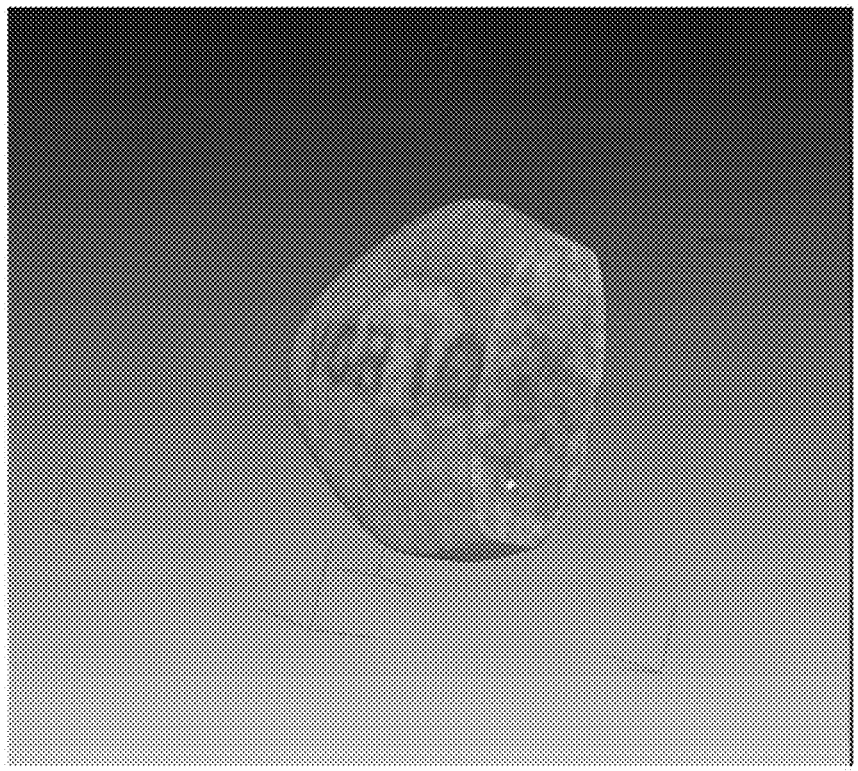

Real and fake tablets were tested and the X-ray diffraction results are shown in FIG. 3. Both tablets contained the same amount of active pharmaceutical ingredient (API) as was confirmed by high performance liquid chromatography (HPLC). Although there are some differences, the determination of a fake tablet using just the X-ray diffraction results is not completely straightforward. However, using the CT scanner, the results shown in FIG. 4, the counterfeit tablet (upper image) clearly shows more inhomogeneities than the genuine tablet (lower image) and is therefore immediately identifiable.

Figure 5:
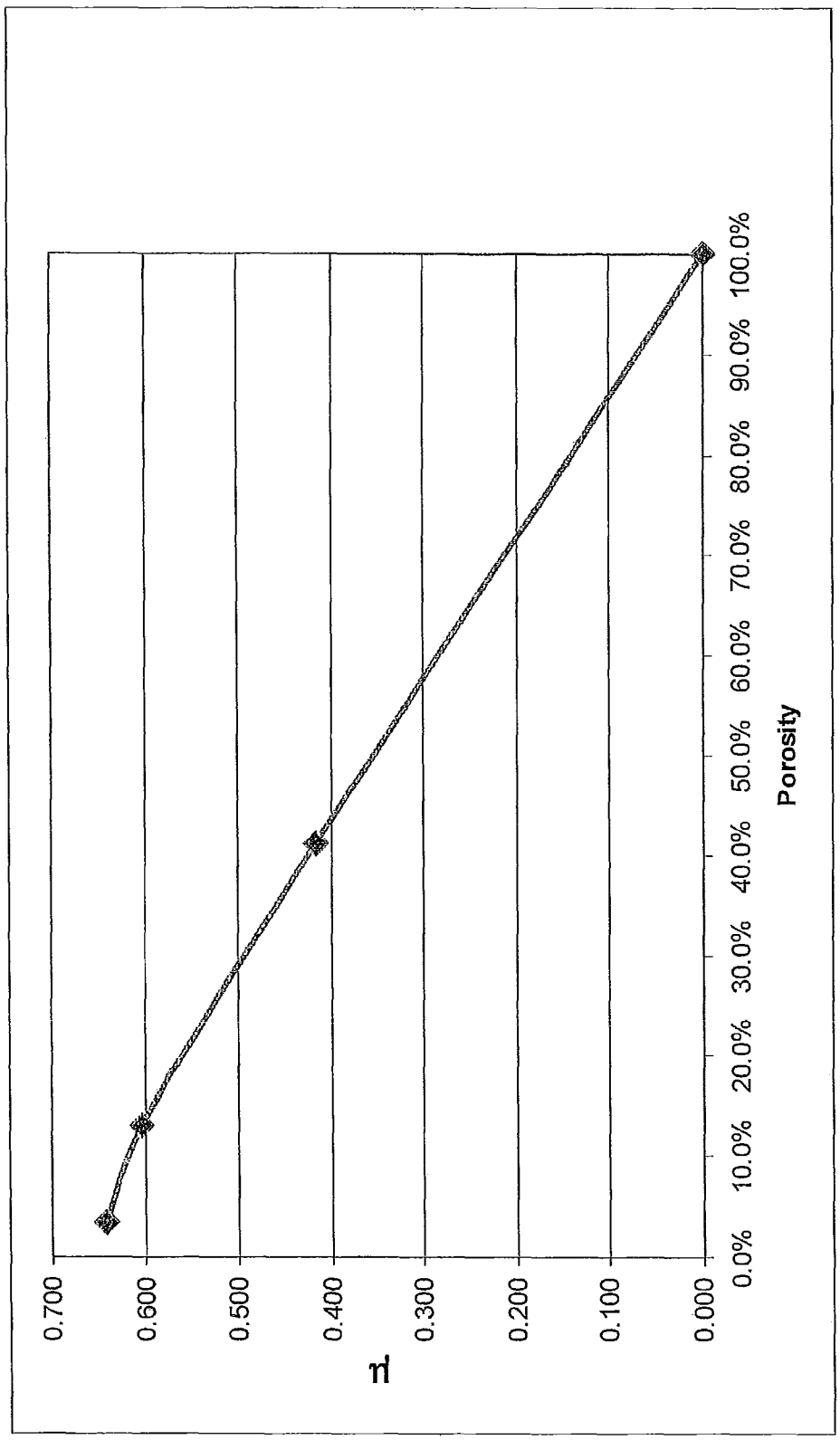
FIG. 5 shows measurements of absorption of a sample of a drug.

Another use is to determine the porosity of pharmaceutical tablets. Tablets of Avicel (registered trade mark) were prepared with different porosity, namely three different values of porosity (the void fraction) $\epsilon$ of 3.5%, 13.1% and 41.2%. The pores in these tablets are too small to normally be resolvable. CT scans were taken from these tablets and the transmission ratio $\mu$, defined as the transmission through the tablet and the total radiation, determined from the results. The transmission ratio $\mu$ gave a good measure of the porosity of the tablets as illustrated in the graph in FIG. 5.

Figure 6:
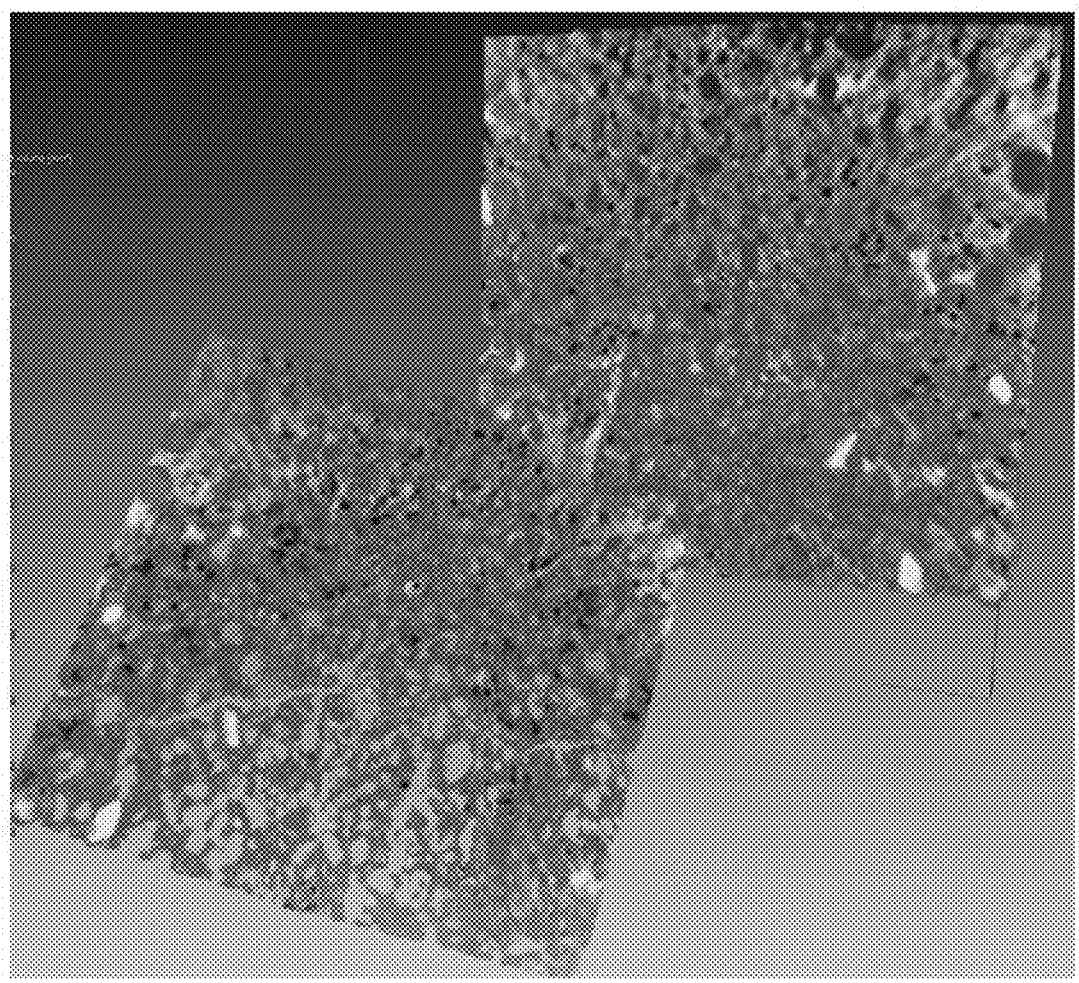
FIG. 6 shows CT images of a concrete sample.

The use of CT in XRD equipment is not only applicable to the field of pharmaceuticals. For example, two samples of concrete were measured, one being a brittle sample and one more stiff and stable. The X-ray diffraction results show some differences in the texture of the calcite and quartz phases. However, this was not enough to clearly distinguish between the samples. Using CT good images of the sample showing the pores could be determined as shown in FIG. 6.

The use of the invention is not, of course, limited to the specific applications described and those skilled in the art will be able to use the invention in a wide variety of applications.

I claim:

1. A dual mode X-ray diffraction and computed tomography imaging system, comprising:
   an X-ray source for emitting an X-ray beam;
   a two-dimensional X-ray detector;
   a sample position;
   a goniometer for positioning the X-ray source, X-ray detector and a sample at the sample position relative to one another; and
   a computer arranged to process the input from the 2D detector and output information about the sample based on the input from the 2D detector and the relative positions of X-ray source, X-ray detector and sample;
   wherein the computer positions the X-ray source, X-ray detector and sample to operate in an X-ray diffraction, XRD, mode carrying out angle dispersive X-ray diffraction on the sample by measuring the X-ray diffraction as a function of diffraction angle $2\theta$ using the X-ray detector; and
   the computer positions the X-ray source, X-ray detector and sample to operate in a computed tomography, CT, mode to measure absorption of a sample as a function of position across the sample with the two-dimensional X-ray detector;
   wherein the imaging system operates in dual XRD mode and CT mode; and
   wherein the X-ray source is a source that emits X-rays having at least 30% of the total emitted X-ray intensity in at least one X-ray line in an energy band in the range 4.5 keV to 25 keV.

2. An imaging system according to claim 1, wherein the X-ray source uses a Cr, Co, Cu, Mo or Ag target.

3. An imaging system according to claim 1 wherein the X-ray detector is a two dimensional photon counting X-ray detector.

4. An imaging system according to claim 1, wherein the imaging system is arranged to operate in the CT mode to capture a plurality of absorption measurements of the absorption of the sample as a function of position across the sample by rotating the sample with respect to the source and detector, and to combine the plurality of measured absorption measurements to produce a CT image.

5. An imaging system according to claim 1 further comprising an integrated unit comprising a rotary sample mount for mounting the sample within 5 cm of the detector.

6. An imaging system according to claim 5 wherein the integrated unit further comprises a rotary drive connected to the sample mount for rotating the rotary sample mount to a plurality of different orientations for a CT measurement in the CT mode.

7. An imaging system according to claim 1 further comprising a beam conditioner arranged adjacent to the X-ray source, the beam conditioner being a pinhole aperture, a slit or an X-ray mirror.

8. An imaging system according to claim 1 further comprising a monochromator.

9. An imaging system according to claim 1, further comprising a beam stop placed in the direct line of the X-ray beam after the sample in the XRD mode, the beam stop being removed in the CT mode.

10. A method of operating an imaging system, comprising:
positioning an X-ray source, X-ray detector and a sample at a sample position relative to one another;
emitting an X-ray beam from the X-ray source towards the sample;
detecting the beam after interaction with a sample using a two-dimensional X-ray detector;
the method including processing the input from the 2D detector and output information about the sample based on the input from the 2D detector and the relative positions of X-ray source, X-ray detector and sample; and
operating the imaging system in an X-ray diffraction, XRD, mode carrying out angle dispersive X-ray diffraction on the sample by measuring the X-ray diffraction as a function of diffraction angle 2θ using the X-ray detector; and
operating the imaging system in a computed tomography, CT, mode measuring absorption of a sample as a function of position across the sample with the two-dimensional X-ray detector;
wherein the imaging system is operated in dual XRD mode and CT mode; and
wherein the X-ray source is a source that emits X-rays having at least 30% of the total emitted X-ray intensity in at least one X-ray line in an energy band in the range 4.5 keV to 25 keV.

11. A method according to claim 10, wherein the X-rays are emitted by a Cr, Co, Cu, Mo or Ag target.

12. A method according to claim 10 including detecting the beam using a two dimensional photon counting X-ray detector.

13. A method according to claim 10 comprising operating in the CT mode by capturing a plurality of absorption measurements of the absorption of the sample as a function of position across the sample by rotating the sample with respect to the source and detector, and combining the plurality of measured absorption measurements to produce a CT image.

14. A method according to claim 13, further comprising mounting the sample on an integrated unit comprising the two-dimensional X-ray detector and a rotary sample mount, mounting the sample within 5 cm of the detector; and
rotating the sample on the rotary sample mount to obtain the plurality of absorption measurements.

* * * * *